United States Patent
Cordaro et al.

(10) Patent No.: US 8,676,311 B2
(45) Date of Patent: *Mar. 18, 2014

(54) MEMORY DEVICE ASSOCIATED WITH DEFIBRILLATION ELECTRODES

(75) Inventors: Marc Cordaro, Sudbury, MA (US); Michael Parascandola, Londonderry, NH (US); Ward Hamilton, Amherst, NH (US); Michael R. Dupelle, N. Attleboro, MA (US); Paul F. Prew, S. Attleboro, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 793 days.

This patent is subject to a terminal disclaimer.

(21) Appl. No.: 12/726,336

(22) Filed: Mar. 17, 2010

(65) Prior Publication Data

US 2011/0054553 A1 Mar. 3, 2011

Related U.S. Application Data

(63) Continuation of application No. 11/481,409, filed on Jul. 5, 2006, now abandoned.

(51) Int. Cl.
*A61N 1/362* (2006.01)

(52) U.S. Cl.
USPC .................................................. 607/5

(58) Field of Classification Search
USPC ..................... 600/41, 390; 607/5, 115
See application file for complete search history.

(56) References Cited

U.S. PATENT DOCUMENTS

| 5,697,955 | A | 12/1997 | Stolte |
| 6,259,939 | B1 | 7/2001 | Rogel |
| 6,390,996 | B1 | 5/2002 | Halperin et al. |
| 6,782,293 | B2 | 8/2004 | Dupelle et al. |
| 2002/0082644 | A1 | 6/2002 | Picardo et al. |
| 2006/0178706 | A1 | 8/2006 | Lisogurski et al. |

FOREIGN PATENT DOCUMENTS

| WO | 97/43000 | 11/1997 |
| WO | 2005/092430 | 10/2005 |

OTHER PUBLICATIONS

Philips Medical Systems Brochure, Heartstart Onsite Defibrillator (2002).

*Primary Examiner* — George Manuel
(74) *Attorney, Agent, or Firm* — Fish & Richardson P.C.

(57) ABSTRACT

An electrode package for use with a defibrillator, the electrode package comprising an outer shell providing a vapor barrier between an interior space inside the outer shell and an exterior environment, one or more defibrillation electrodes positioned in the interior space inside the outer shell, each of the defibrillation electrodes including a metallic layer in electrical contact with a conductive liquid-containing layer through which electrical current is delivered to a patient when the defibrillation electrodes have been applied to the patient, the conductive a liquid-containing layer being subject to drying out as liquid from the water-containing layer vaporizes and travels from the interior space to the external environment, and one or more electrical conductors extending from inside of the outer shell to a package electrical connector outside of the shell, the package electrical connector being configured to be connected to a mating defibrillator electrical connector connected to the defibrillator, and an electronic memory device positioned outside the outer shell and in electrical contact with some of the electrical conductors extending from the outer shell to the package electrical connector.

22 Claims, 12 Drawing Sheets

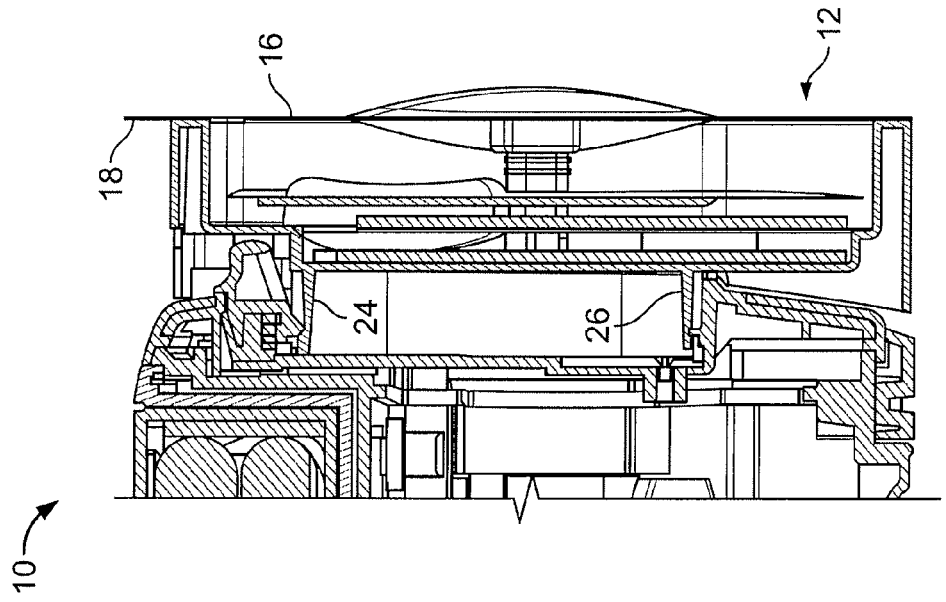
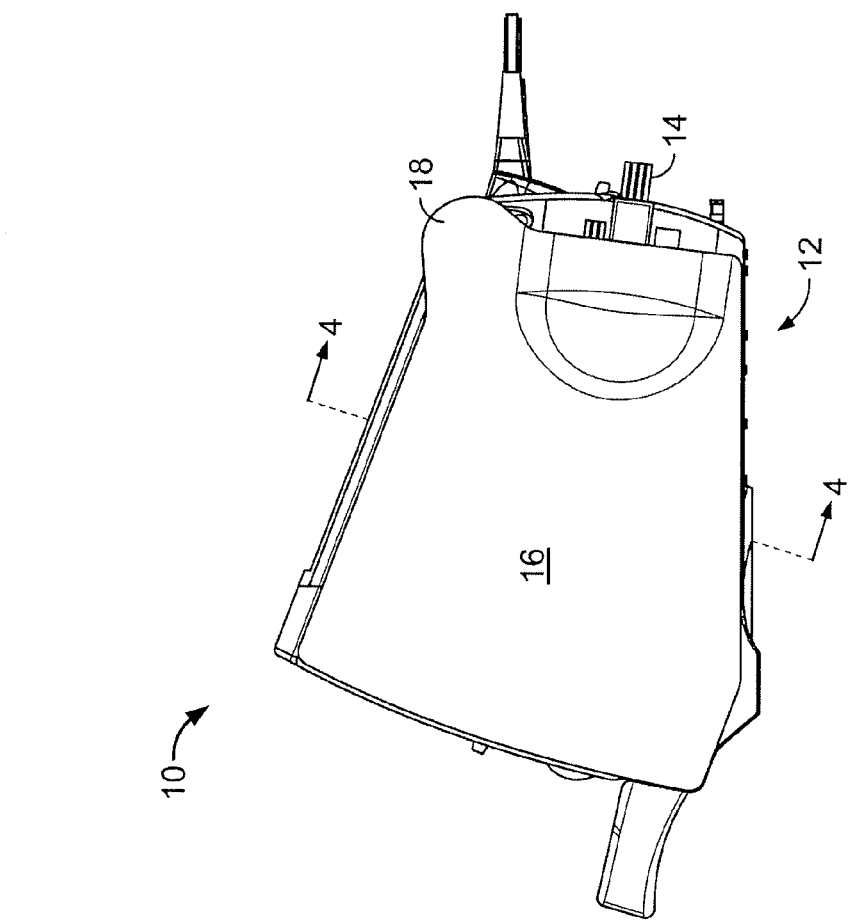
FIG. 4
FIG. 3

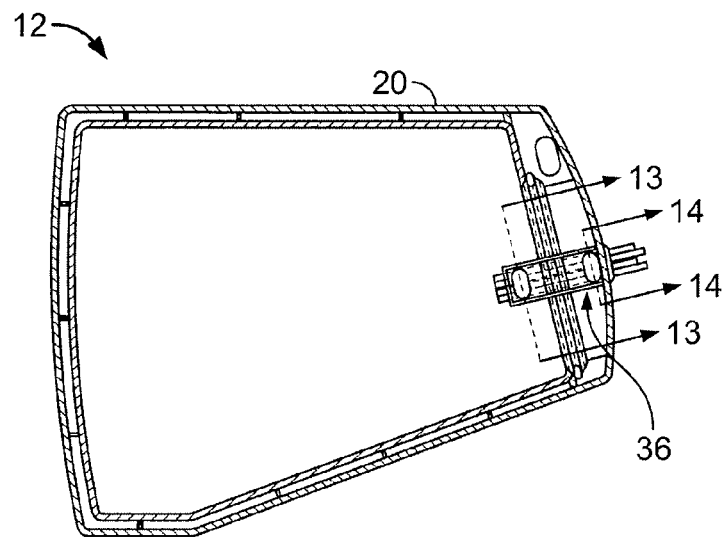
FIG. 12
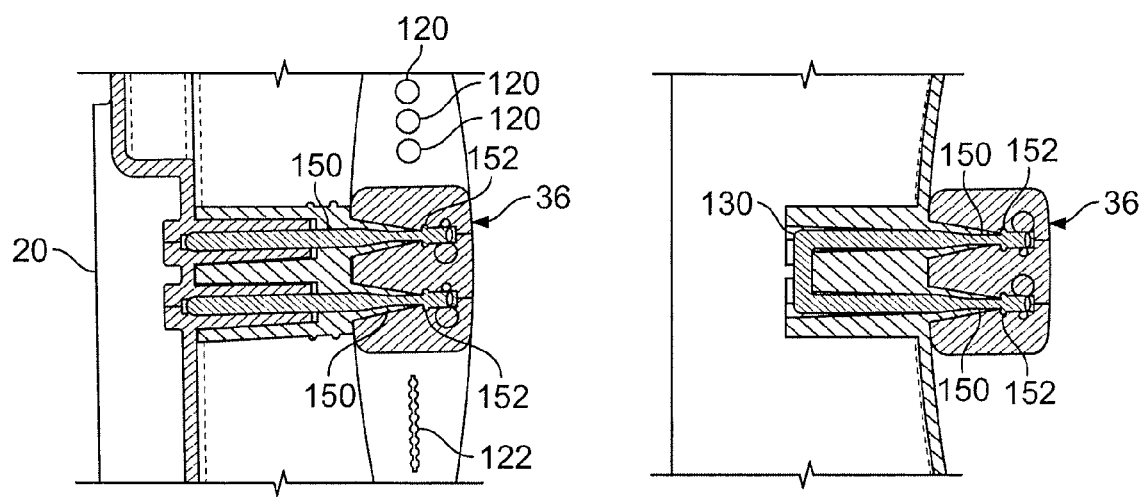
FIG. 13
FIG. 14

MEMORY DEVICE ASSOCIATED WITH DEFIBRILLATION ELECTRODES

CROSS-REFERENCE TO RELATED APPLICATION

This application is a continuation application of and claims priority to U.S. application Ser. No. 11/481,409, filed on Jul. 5, 2006 now abandoned. This application is hereby incorporated by reference.

TECHNICAL FIELD

This invention relates to defibrillation electrodes.

BACKGROUND

There is a growing trend toward the replacement of multiple use defibrillator paddles with single-use disposable therapeutic electrodes for defibrillation, external transthoracic pacing, or the combination of both. This trend is driven by numerous factors including, but not limited to: (1) convenience related to not having to apply a conductive media (e.g., gel), (2) speed of care when switching from delivering a defibrillation shock to a pacing current, (3) caregiver safety in that contact with the patient can be avoided as the therapy can be delivered remotely from the host device, and (4) increased use of defibrillators incorporating algorithms that analyze the presented ECG rhythm for appropriateness of therapeutic (shock) delivery. These applications typically work only with single-use, disposable therapeutic electrodes.

Defibrillation of cardiac arrest is a time sensitive matter. It is well documented that for every minute delivery is delayed, the chance of survival falls 7 to 10 percent. One way manufacturers have addressed the time to shock issue, has been to create electrodes that can be pre-connected to a defibrillator. If electrodes are not pre-connected or present, valuable time will be lost, and chance of survival diminished as responders must address this matter.

Owing to many factors both chemical and environmental in nature, single-use therapeutic electrodes have a finite shelf life. Manufacturers typically label individual electrodes with specific dates of expiration beyond which therapeutic delivery cannot be insured. It is incumbent on the operator to read the electrode labeling prior to use to insure a non-expired electrode is deployed for therapy.

Electrode packaging is designed to be both airtight and watertight. This is to minimize environmental fluctuations that might shorten the useful life of an electrode. Should an electrode package be breached, chemical reactions will be accelerated and shelf life shortened.

Checking for the condition of an electrode package, or reading the expiration date are time consuming are potential points of error that have the potential to adversely affect a defibrillator's therapeutic capabilities.

SUMMARY

In a first aspect, the invention features an electrode package for use with a defibrillator, the electrode package comprising an outer shell providing a vapor barrier between an interior space inside the outer shell and an exterior environment, one or more defibrillation electrodes positioned in the interior space inside the outer shell, each of the defibrillation electrodes including a metallic layer in electrical contact with a conductive liquid-containing layer through which electrical current is delivered to a patient when the defibrillation electrodes have been applied to the patient, the conductive liquid-containing layer being subject to drying out as liquid from the water-containing layer vaporizes and travels from the interior space to the external environment, and one or more electrical conductors extending from inside of the outer shell to a package electrical connector outside of the shell, the package electrical connector being configured to be connected to a mating defibrillator electrical connector connected to the defibrillator, and an electronic memory device positioned outside the outer shell and in electrical contact with some of the electrical conductors extending from the outer shell to the package electrical connector.

Preferred implementations of this aspect of the invention may incorporate one or more of the following. The memory device may be configured to store an expiration date for the electrode package. The memory device may be positioned within the interior of the package electrical connector. The memory device may be configured to store information indicative of a condition sensor voltage level at which the electrode may not be suited for defibrillation. The information stored by the memory device may comprise a voltage threshold indicative of a limit on the acceptable electrical potential of an electrochemical cell within the electrode package. The memory device may be configured to store an indication of whether the two defibrillation electrodes are therapeutic electrodes for use in delivery of defibrillation pulses or for use in training in the use of the defibrillator. The memory device may be configured to store information that when read by the defibrillator can change the user interface or display provided the user of the defibrillator. The memory device may be configured to store information indicative of the configuration of components inside the electrode package. The configurations identified by the information may comprise: defibrillation electrodes only, defibrillation electrodes with ECG monitoring electrodes, defibrillation electrodes with CPR puck, and defibrillation electrodes with ECG monitoring electrodes and CPR puck. The information may be indicative of prompts that should be delivered to the user. The memory device may be configured to store information specifying a type of defibrillation electrode, wherein the type may comprise whether the electrode is an adult or pediatric electrode.

In a second aspect, the invention features an electrode package for use with a defibrillator, the electrode package comprising an outer shell providing a vapor barrier between an interior space inside the outer shell and an exterior environment, one or more defibrillation electrodes positioned in the interior space inside the outer shell, each of the defibrillation electrodes including a metallic layer in electrical contact with a conductive liquid-containing layer through which electrical current is delivered to a patient when the defibrillation electrodes have been applied to the patient, the conductive liquid-containing layer being subject to drying out as liquid from the water-containing layer vaporizes and travels from the interior space to the external environment, and one or more electrical conductors extending from inside of the outer shell to a package electrical connector outside of the shell, the package electrical connector being configured to be connected to a mating defibrillator electrical connector connected to the defibrillator, and an electronic memory device in electrical contact with some of the electrical conductors, wherein the memory device is configured to store information specifying a type of defibrillation electrode, wherein the type comprises whether the electrode is an adult or pediatric electrode.

Preferred implementations of this aspect of the invention may incorporate one or more of the following. The memory device may be further configured to store an indication of the configuration of components stored in the package. The memory device may be further configured to store an expiration date for the electrode package.

In a third aspect, the invention features an electrode package for use with a defibrillator, the electrode package comprising an outer shell providing a vapor barrier between an interior space inside the outer shell and an exterior environment, one or more defibrillation electrodes positioned in the interior space inside the outer shell, each of the defibrillation electrodes including a metallic layer in electrical contact with a conductive liquid-containing layer through which electrical current is delivered to a patient when the defibrillation electrodes have been applied to the patient, the conductive liquid-containing layer being subject to drying out as liquid from the water-containing layer vaporizes and travels from the interior space to the external environment, and one or more electrical conductors extending from inside of the outer shell to a package electrical connector outside of the shell, the package electrical connector being configured to be connected to a mating defibrillator electrical connector connected to the defibrillator, and an electronic memory device in electrical contact with some of the electrical conductors, wherein the memory device is configured to store information indicative of a voltage limit on the voltage output of a condition sensor indicating the functionality of the electrode.

Preferred implementations of this aspect of the invention may incorporate one or more of the following. The information stored by the memory device may comprise information indicative of a limit on an electrical potential of an electrochemical cell within the electrode package.

In a fifth aspect, the invention features a defibrillator for providing a defibrillation pulse to electrodes applied to the chest of a patient, the defibrillator comprising a pair of electrical outputs for delivering the defibrillation pulse to a pair of defibrillation electrodes, processing circuitry and associated software for controlling the defibrillator, including delivery of the defibrillation pulse, an electrical energy storage element for storing the energy delivered in the defibrillation pulse, a user interface element or elements connected to the processing circuitry for accepting one or more inputs from the user and communicating one or more pieces of information to the user, and a housing containing the storage element, processing circuitry, user interface, and providing at its exterior the pair of electrical outputs, wherein the processing circuitry and associated software are configured to read the content of a memory device external to the defibrillator and associated with the pair of defibrillation electrodes, wherein the content comprises information specifying a type of defibrillation electrode, wherein the type comprises whether the electrode is an adult or pediatric electrode, and wherein the processing circuitry and associated software are configured to alter the energy level of the defibrillation pulse based on the type read from the memory device.

In a sixth aspect, the invention features a defibrillator for providing a defibrillation pulse to electrodes applied to the chest of a patient, the defibrillator comprising a pair of electrical outputs for delivering the defibrillation pulse to a pair of defibrillation electrodes, processing circuitry and associated software for controlling the defibrillator, including delivery of the defibrillation pulse, an electrical energy storage element for storing the energy delivered in the defibrillation pulse, a user interface element or elements connected to the processing circuitry for accepting one or more inputs from the user and communicating one or more pieces of information to the user; and a housing containing the storage element, processing circuitry, user interface, and providing at its exterior the pair of electrical outputs, wherein the processing circuitry and associated software are configured to read the content of a memory device external to the defibrillator and associated with the pair of defibrillation electrodes, and wherein the content of the memory device is indicative of a limit on an electrical potential of a condition sensor within the electrode package.

Preferred implementations of this aspect of the invention may incorporate one or more of the following. The limit may represent a limit on the voltage output of the condition sensor for which a defibrillation pulse should be delivered. The condition sensor may comprise an electrochemical cell and the limit may represent the minimum electrical potential of the electrochemical cell. The processing circuitry and associated software may be configured to compare a measured potential to the limit to call for delivery of a warning indication to the user based on the outcome of a comparison, wherein the warning indication may inform the user that the defibrillation electrodes should be replaced.

In a seventh aspect, the invention features a defibrillator for providing a defibrillation pulse to electrodes applied to the chest of a patient, the defibrillator comprising a pair of electrical outputs for delivering the defibrillation pulse to a pair of defibrillation electrodes, processing circuitry and associated software for controlling the defibrillator, including delivery of the defibrillation pulse, an electrical energy storage element for storing the energy delivered in the defibrillation pulse, a user interface element or elements connected to the processing circuitry for accepting one or more inputs from the user and communicating one or more pieces of information to the user; and a housing containing the storage element, processing circuitry, user interface, and providing at its exterior the pair of electrical outputs, wherein the processing circuitry and associated software are configured to read the content of a memory device external to the defibrillator and associated with the pair of defibrillation electrodes, and wherein the content of the memory device is indicative of a user interface or prompt that should be provided to the user.

Among the many advantages of the invention (some of which may be achieved only in some of its various aspects and implementations) are the following: Locating the memory device outside of the electrode package removes it from a humid and corrosive environment, thus improving reliability, and this may simplify manufacturing. Including the various other types of information in the storage of the memory device improves the functionality and performance of the defibrillator.

Other features and advantages of the invention will be found in the detailed description, drawings, and claims.

DESCRIPTION OF DRAWINGS

FIG. 3 is a side elevation view of the defibrillator of FIG. 1 looking toward the side with the electrode package.

FIG. 4 is a cross-sectional view taken along section 4-4 in FIG. 3.

FIG. 12 is a plan view showing the rigid shell of the electrode package with its removable lid removed and its contents removed.

FIG. 13 is a partial cross-sectional view taken along section B-B in FIG. 12 showing a cross section through an inner end of the gasket element of the electrode package.

FIG. 14 is a partial cross-sectional view taken along section A-A in FIG. 12 showing a cross section through an outer end of the gasket element of the electrode package.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
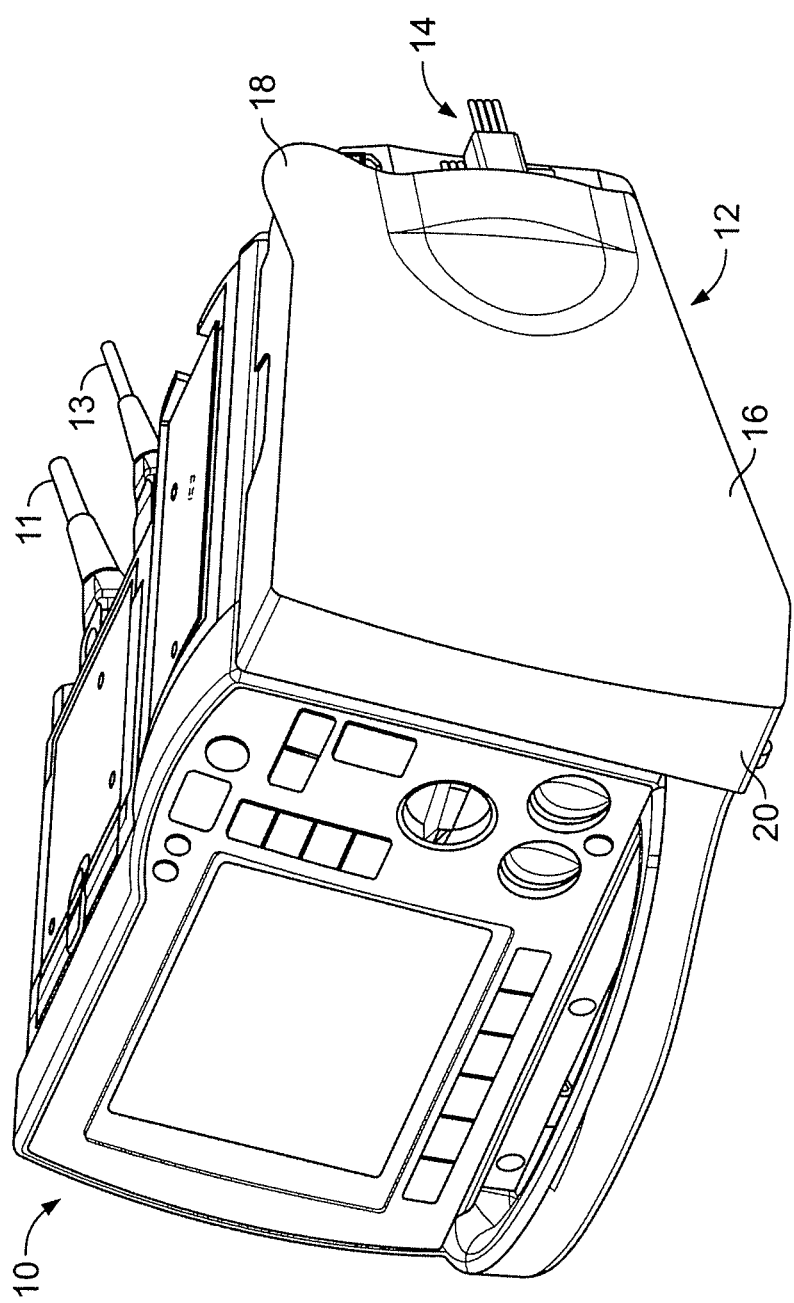
FIG. 1 is a perspective view of a defibrillator implementation of the invention.
Figure 2:
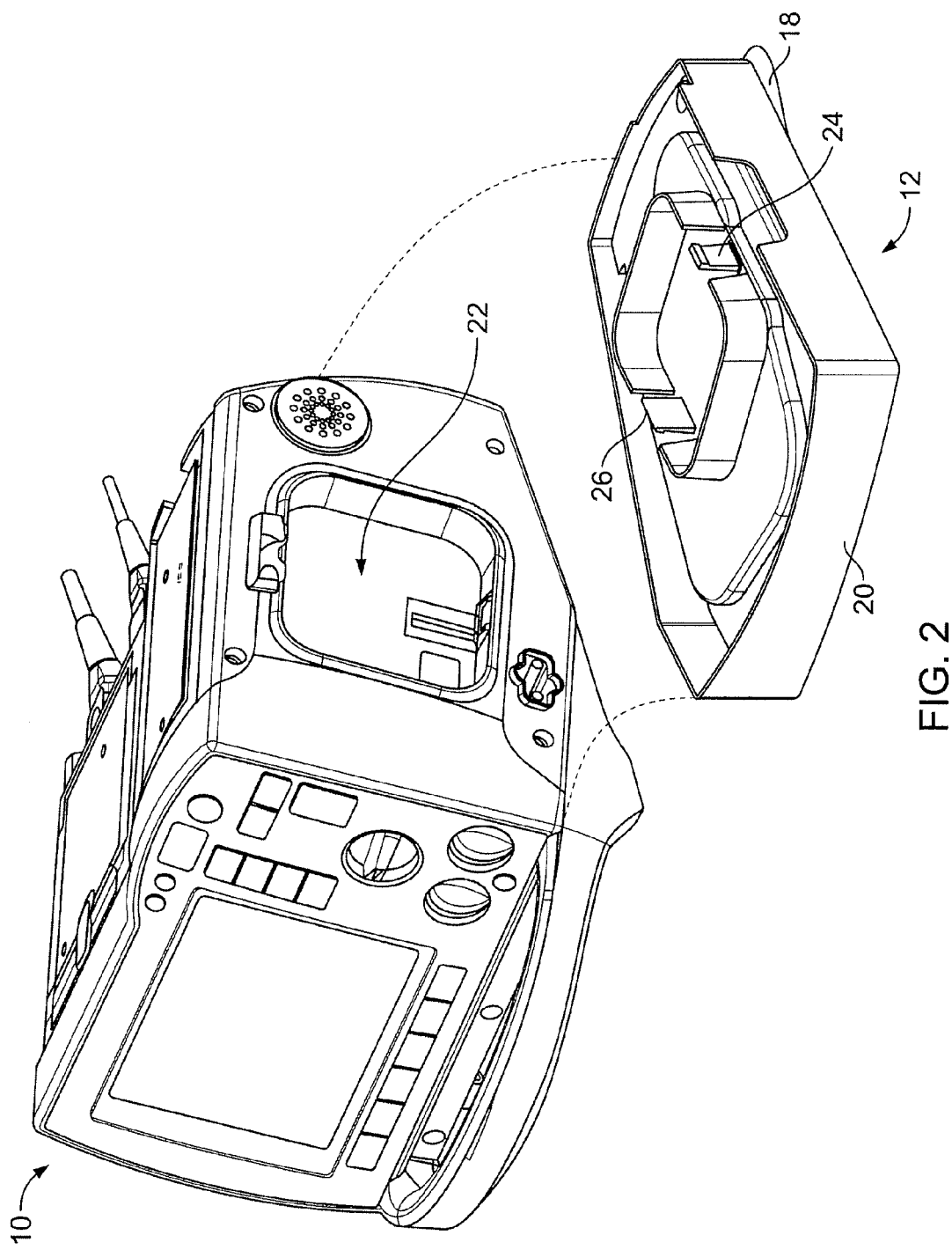
FIG. 2 is a perspective view of the defibrillator of FIG. 1 with an electrode package shown removed.

FIGS. 1-4 show an external defibrillator 10 (e.g., a hospital crash cart defibrillator, such as the R Series manufactured by ZOLL Medical of Chelmsford, Massachusetts). User interface elements (graphical display, speaker, microphone, input buttons and dials) are provided on the front face of the defibrillator. Attached to the right side of the defibrillator is an electrode package 12, which is removable from the defibrillator, as shown in FIG. 2, and normally electrically connected to the defibrillator by cable 14 even when the defibrillator is not in use. The multi-conductor cable 14 emerging from the electrode package passes through a connector (not shown in FIGS. 1-4, but shown in the schematic of FIG. 11) and divides into two cables 11, 13 which attach to the back of the defibrillator. A removable lid 16 is removed (by grasping tab 18) to open the defibrillator package.

The electrode package 12 includes a rigid base (or tray) 20 (polypropylene), which with the removable lid 16 (foil lined paper) constitutes the outer shell of the package. The base and lid provide a moisture barrier to prevent the gel layers of the electrodes from drying out during the shelf life of the package. The lid is heat sealed to the perimeter of the base (tray). The rigid base (a molded polymer part) is removable snapped into the receptacle 22 on the side of the defibrillator also used to secure a defibrillator paddle. Upper and lower flexible clips 24, 26 snap into engagement with mating elements of the receptacle 22. Engagement of the flexible clips 24, 26 is shown in the cross section of FIG. 4, which shows the electrode package snapped into place on the side of the defibrillator.

Figure 5:
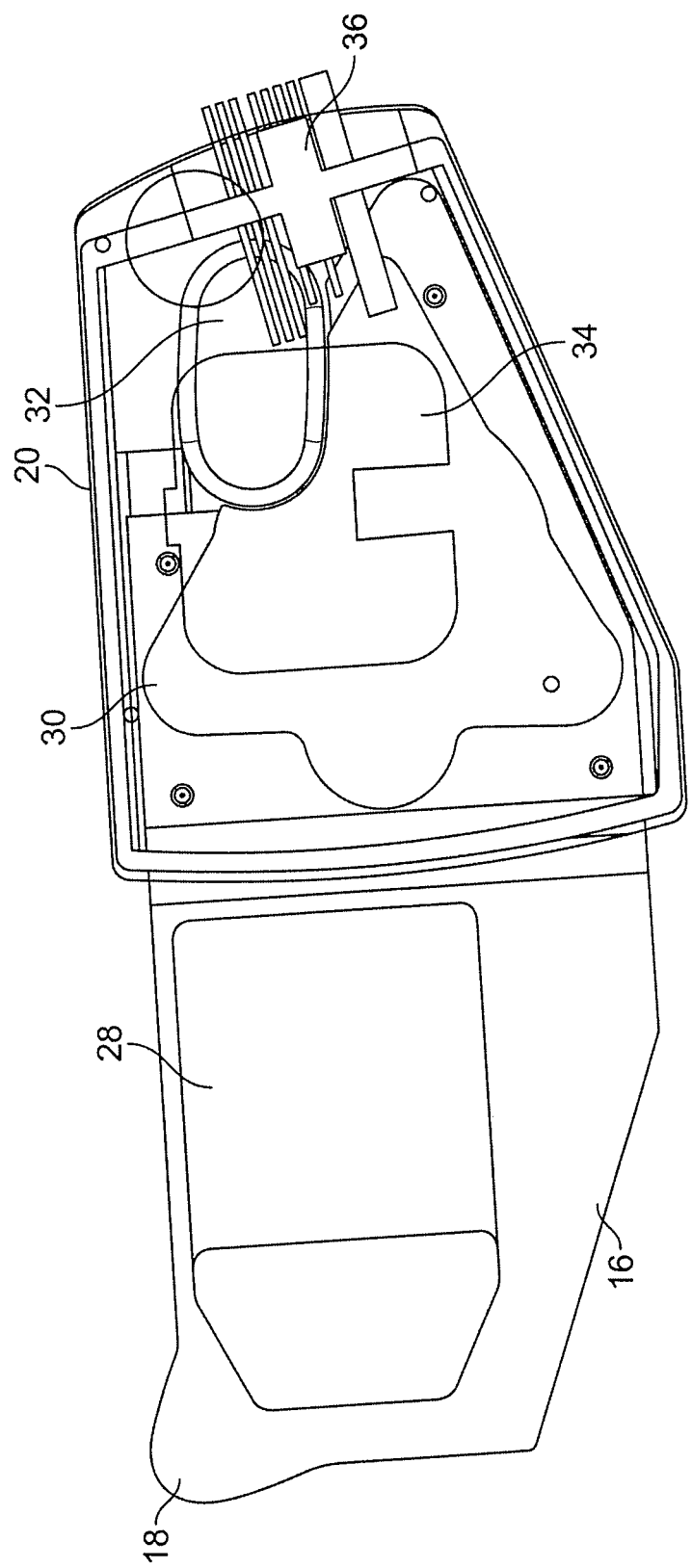
FIG. 5 is a plan view of the electrode package after being opened to expose its contents.

FIG. 5 shows the electrode package with lid 16 peeled back to expose the contents of the package. A first defibrillation electrode 28 (generally square in this plan view) for the back (posterior) of the patient's chest is adhered to a release liner (not shown) secured to the inside face of lid 16. Electrode 28 is peeled off of the release liner and adhered to the back of the chest.

A second defibrillation electrode 30 (generally triangular in this plan view) for the front (anterior) of the patient's chest is adhered to another release liner (not shown) secured to the rigid based of the electrode package. Electrode 30 is an assembly of a defibrillation electrode and three ECG monitoring electrodes, and is described in co-pending U.S. patent application Ser. No. 11/055,572, filed on Feb. 11, 2005, hereby incorporated by reference.

A device for assisting CPR, known as a CPR puck or pad 32, is also stored within the electrode package. A similar CPR pad is described in U.S. Pat. No. 6,782,293, hereby incorporated by reference. It includes an accelerometer for measuring movement of the chest during CPR.

The fourth element within the electrode package is a condition sensor 34 that assists the defibrillator in determining whether the liquid-containing (gel) layers of the defibrillation electrodes are still sufficiently moist to function properly. The condition sensor 34 is not intended to be removed from the package, as it is not used during defibrillation.

Various electrical conductors pass into the electrode package to connect the contents with the defibrillator. These conductors pass through a gasket element 36 that is sealed between the rigid base 20 and removable lid 16 of the package. When the electrodes and CPR puck are removed from the package, the gasket element is also removed, as the electrical conductors for the electrodes and CPR puck extend through the gasket element.

Figure 6:
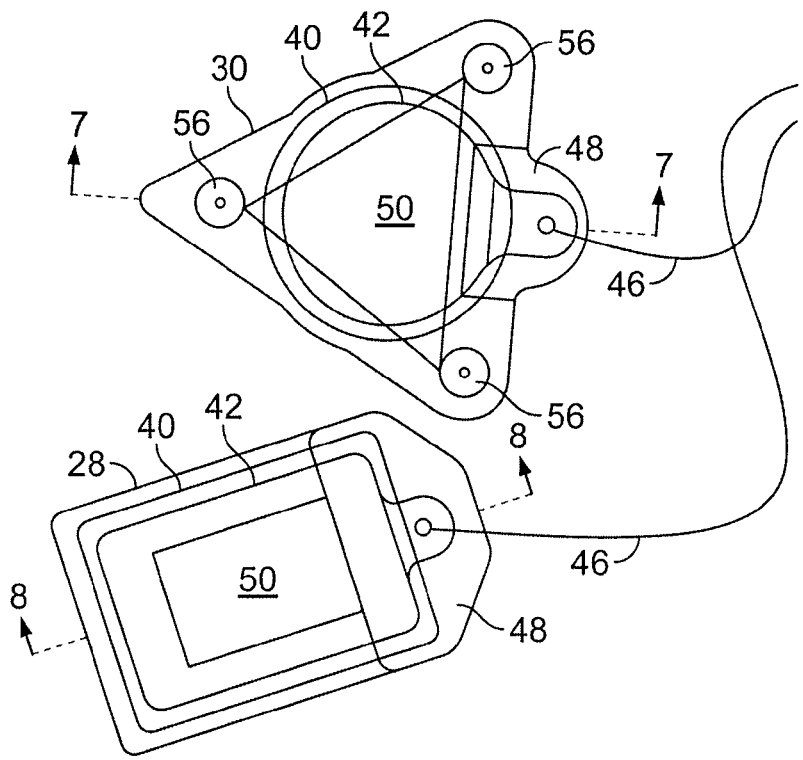
FIG. 6 is a plan view of the two defibrillation electrodes stored inside the electrode package.
Figure 7:
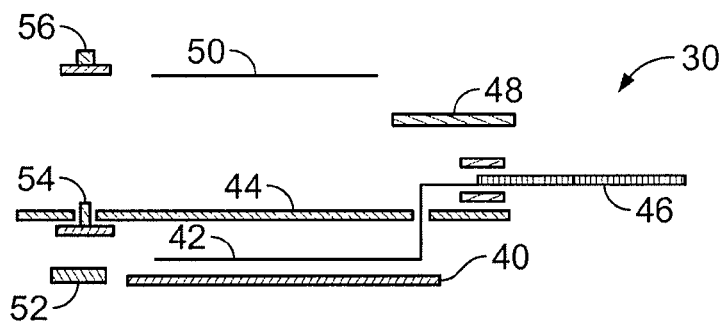
FIG. 7 is an exploded, cross-sectional view taken along 7-7 in FIG. 6.
Figure 8:
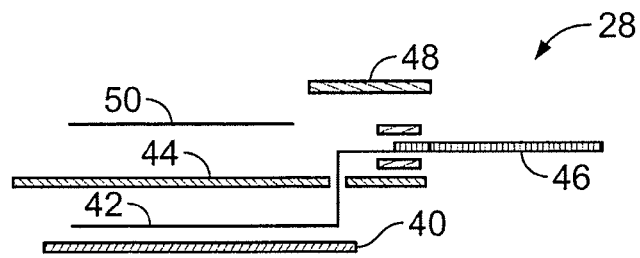
FIG. 8 is an exploded, cross-sectional view taken along 8-8 in FIG. 6.

FIGS. 6-8 show the two defibrillation electrodes 28, 30 in greater detail. The triangular front electrode 30 is shown in FIGS. 6-7. The construction of the electrode is shown in exploded, cross-sectional view in FIG. 7. A conductive liquid-containing layer 40 (solid gel) contacts the patient's skin, and conveys electrical current from the metallic layer 42 (tin plate or other metallic material such as silver chloride) to the patient. The gel and tin layer are supported on foam layer 44, which carries adhesive to secure the electrode to the patient. The metallic layer is connected to wire 46 through which the defibrillation pulse is delivered from the defibrillator. A foam insulator layer 48 covers the area where the metallic layer and wire emerge from the electrode. A label 50 is applied over the foam layer 44.

Figure 21:
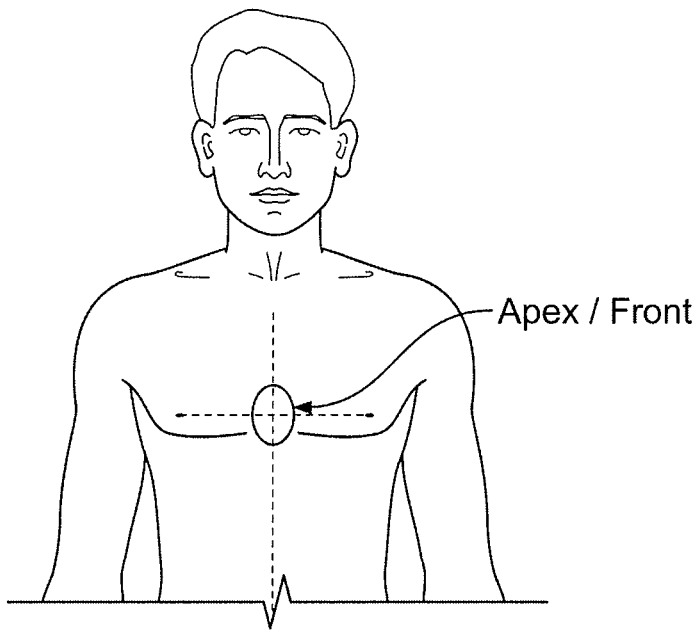
FIG. 21 is a plan view showing the triangular electrode of FIGS. 6-7 applied to a chest of a patient.
Figure 22:
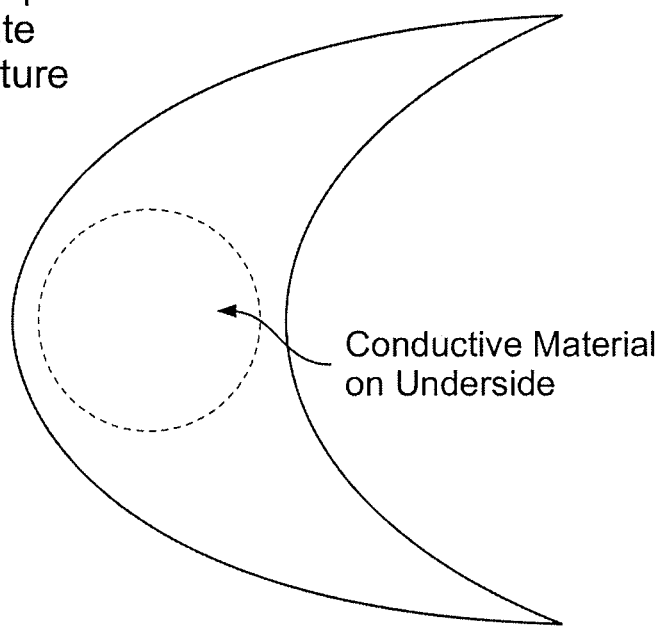
FIG. 22 is a plan view showing an alternative, crescent shaped electrode that could be used in place of the triangular electrode.

FIG. 21 shows the triangular electrode in place on the chest of the patient. The triangular shape greatly facilitates application of the electrode to the chest in the vicinity of a breast. The front electrode is adhered at the edge of the patient's breast, and the triangular shape has an advantage over circular or square electrodes in this location. These other shapes tend to fold or roll back on themselves. E.g., with a square electrode in this location, one corner of the electrode rides up on the breast, and will tend to roll back off the breast. This also tends to occur with circular electrodes. But with the triangular shape the problem is usually avoided. Another shape that will work well is a crescent shape, as shown in FIG. 22, with the smaller radius of the crescent closest to the breast. It is the lateral perimeter of the electrode that has the triangular or crescent shape.

Three ECG monitoring electrodes are built into the three corners of the electrode. Each monitoring electrode includes a solid gel layer 52 for contacting the patient, a conductive stud 54 (Ag/Cl) in contact with the gel layer, and conveying electrical potentials from the gel layer to the snap conductor 56 (Ni/Brass) to which a monitoring wire is connected. Alternatively, the snap conductor can be eliminated, and the ECG monitoring wires connected directly to the conductive studs 54.

The square defibrillation electrode 28 is shown in exploded, cross-sectional view in FIG. 8. It includes most of the same layers as the other defibrillation electrode (identified in the figure by using the same reference numeral for corresponding parts).

Figure 9:
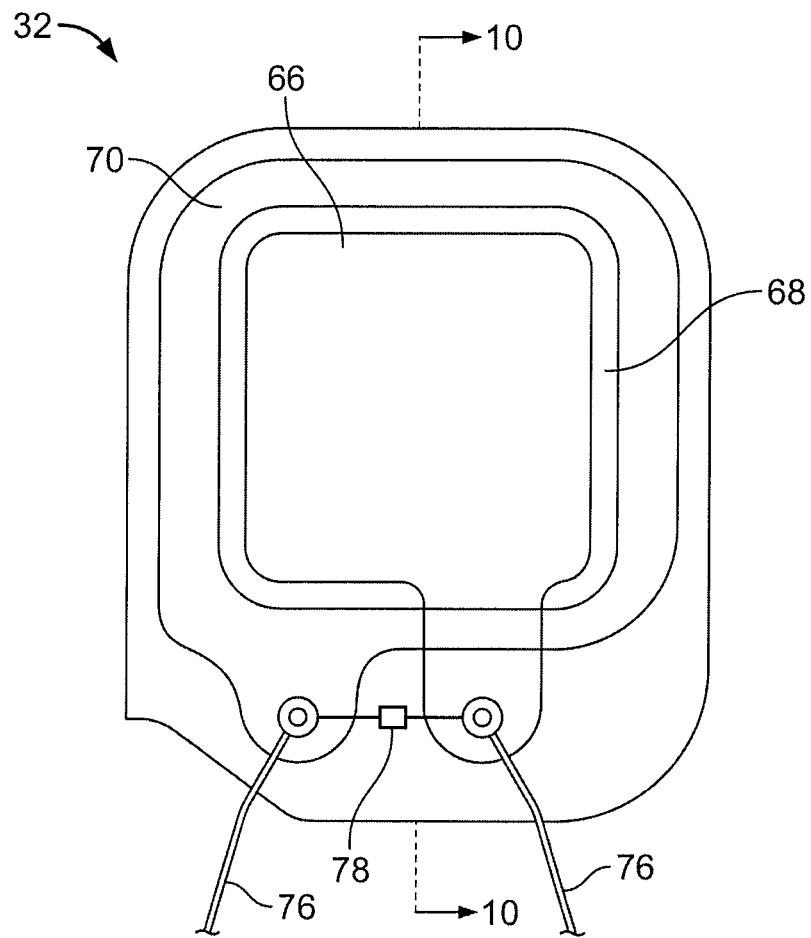
FIG. 9 is a plan view of the condition sensor (electrochemical cell) secured inside the electrode package.
Figure 10:
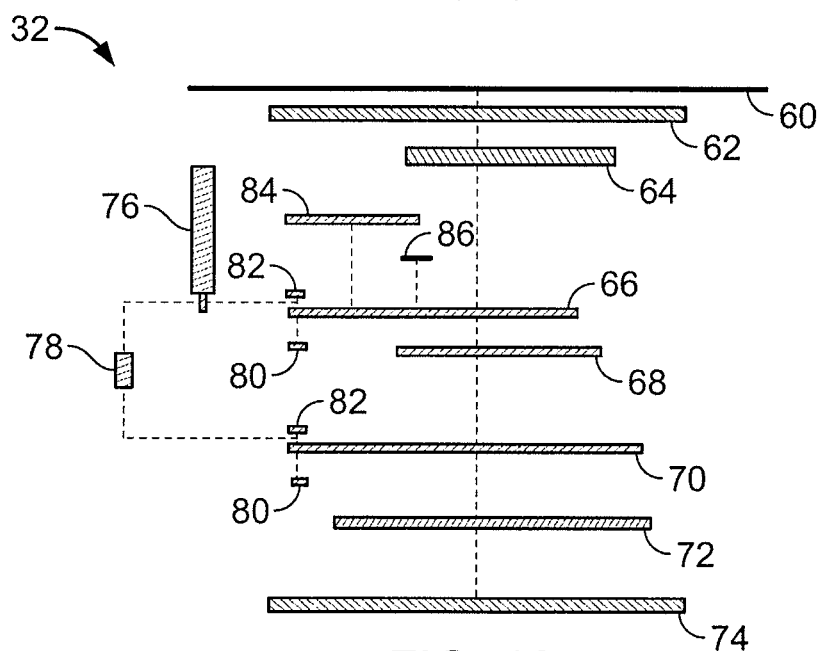
FIG. 10 is an exploded, cross-sectional view taken along section 10-10 in FIG. 9.

FIGS. 9-10 show the condition sensor 32, which functions as an electrochemical cell producing an electrical potential that is measured by the defibrillator to determine whether the moisture in the aqueous layer of the sensor has dried out. As the aqueous layer dries out (because moisture has escaped from the electrode package, e.g., because the package has been damaged), the potential of the electrochemical cell will fall off in magnitude. Once it falls below a threshold, indicating that the aqueous layer of the sensor has dried out, the defibrillator concludes that there is a high probability that the liquid-containing layers of the defibrillation electrodes have also dried out, and a warning prompt is delivered and the defibrillator may not deliver a defibrillation pulse to the electrodes.

Various other alternative tests could be applied to decide that the electrode is no longer suited for its intended use. E.g., the potential could be sampled frequently enough to establish a rate of change, and too high a rate of change could be a basis for deciding that something is wrong with the electrode. Depending on the circuitry used to measure the potential, a problem with the electrode could be detected by a voltage exceeding a threshold, and there could be multiple limits that the measured voltage is tested against.

FIG. 10 shows an exploded, cross-sectional view of the condition sensor. At the top of the stack of layers is a styrene release liner 60, which is removed when the sensor is installed in the electrode package, to expose adhesive on the vinyl mask layer 62, which is adhered to an interior surface of the electrode package to secure the condition sensor within the package. A aqueous layer 64 (gel) is positioned below the vinyl mask. A first metallic layer (metallic element) 66 (tin) is in contact with the gel. That is followed by an insulator layer 68 that is larger in area than the tin layer. Following the insulator layer is a second metallic layer (metallic element) 70 (aluminum) that is also in contact with the gel along its periphery outside of the extent of the insulator layer 68. A foam backing layer 72 and foam cover 74 complete the sandwich of layers. A wire 76 (electrical conductor) is connected to each of the metallic layers (both shown in FIG. 9; one shown in FIG. 10). A bridging resistor 78 (approximately 100K ohms) is connected across the two metallic layers to control the rate of the electrochemical reaction (the size of this resistor will vary with the metals and gels used in the electrochemical cell and with other factors well known to those skilled in the art). The wires 76 are connected to the metallic layers with rings 80 and sockets 82. A foam insulator layer 84 and length of tape 86 are positioned between the aqueous layer 64 and the first metallic layer 66.

Figure 11:
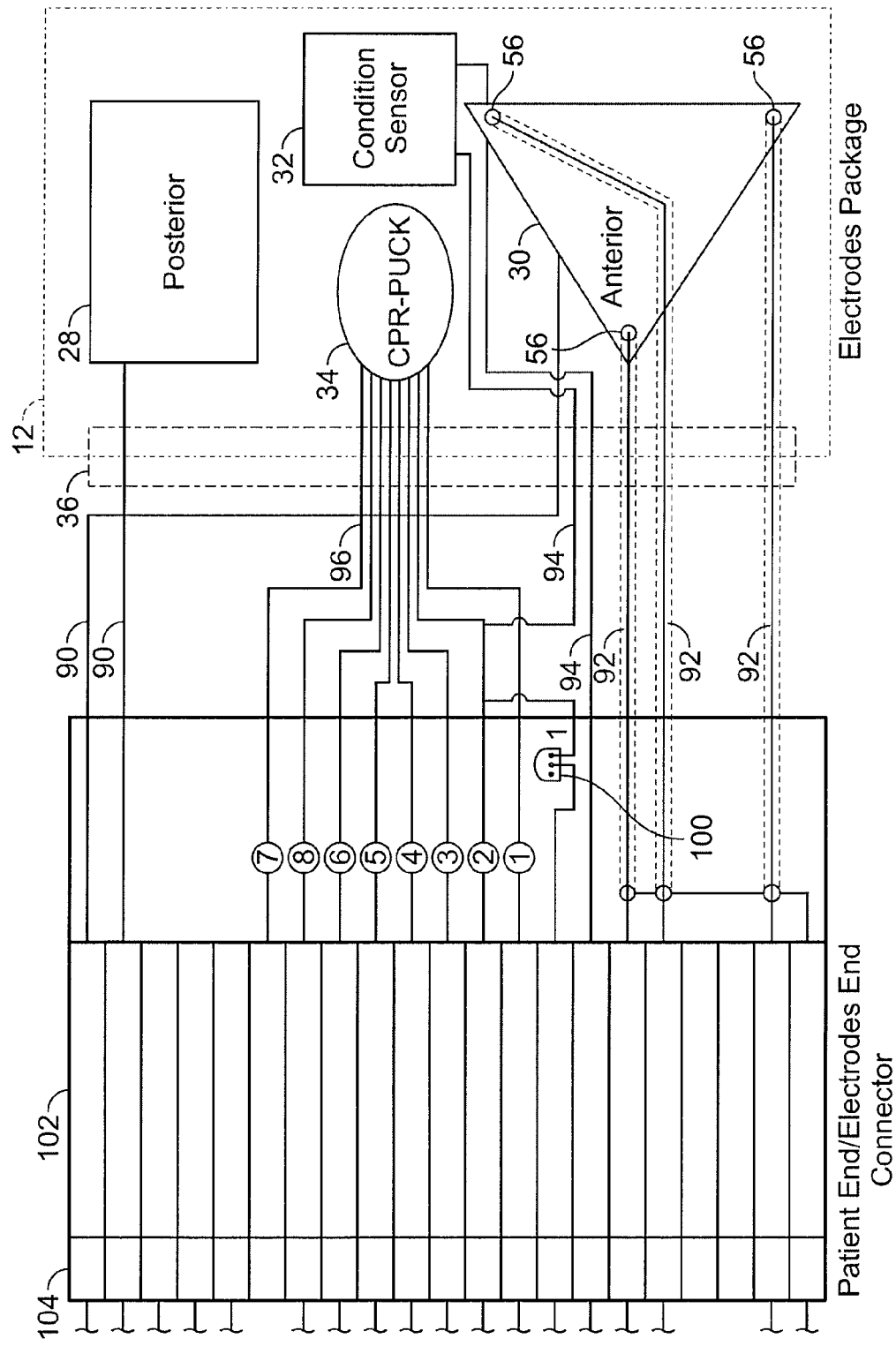
FIG. 11 is a schematic view of the electrical connections between the contents of the electrode package (electrodes, condition sensor, CPR puck) and the electrode package connector.
Figure 15:
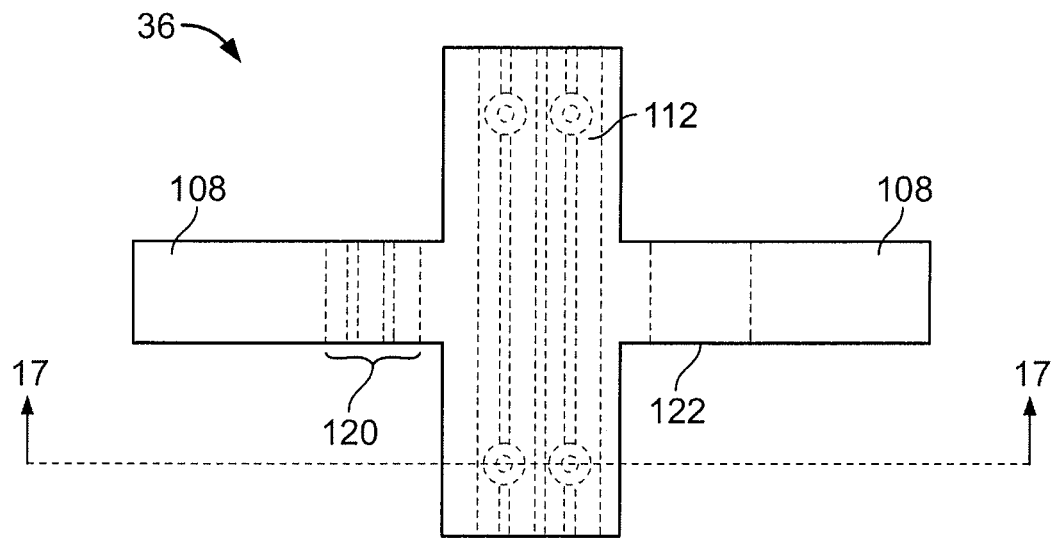
FIG. 15 is a plan view of the gasket element.
Figure 16:
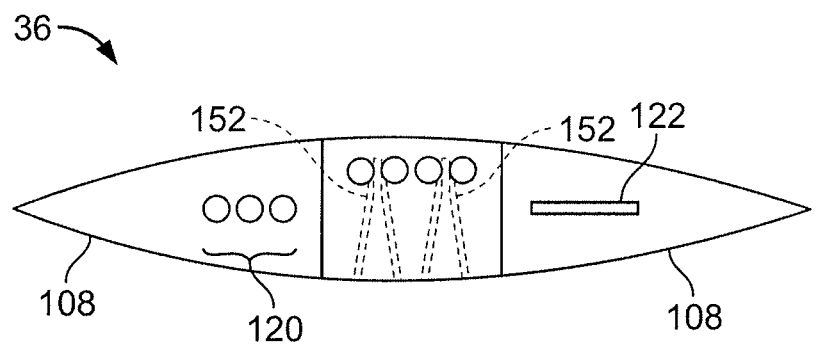
FIG. 16 is an end view of the gasket element.
Figure 17:
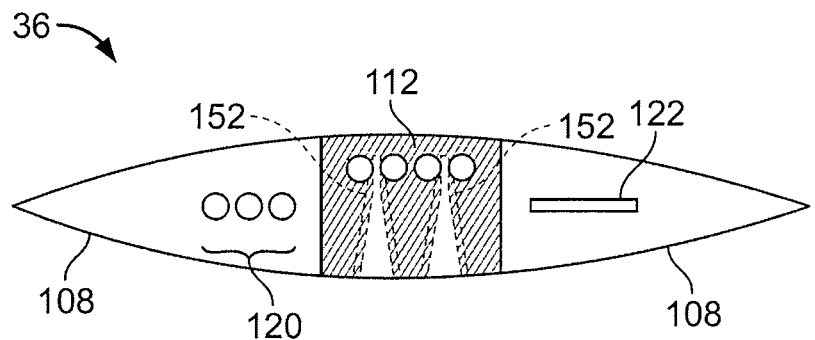
FIG. 17 is a cross-sectional view taken along section 17-17 in FIG. 15.
Figure 18:
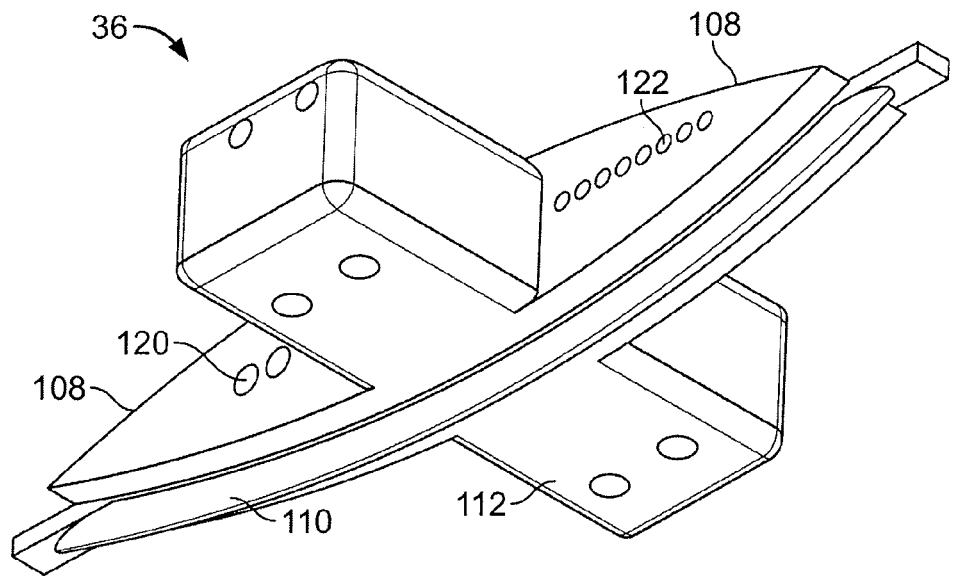
FIG. 18 is a perspective view of the gasket element.
Figure 19:
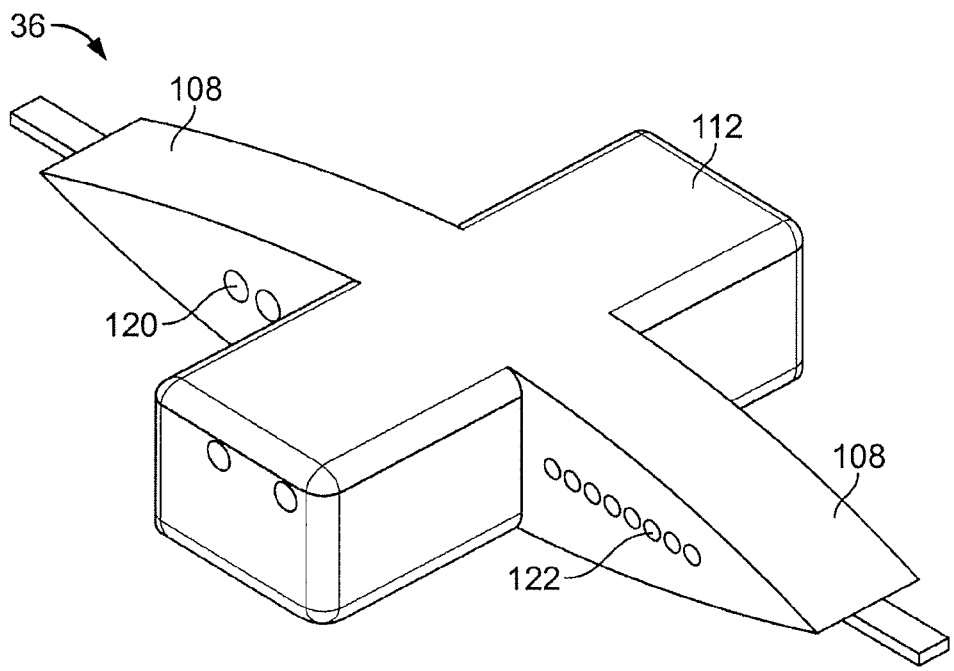
FIG. 19 is another perspective view of the gasket element.

FIG. 11 is an electrical schematic of the electrode package 12. Defibrillator electrodes 28, 30, condition sensor 32, and CPR puck 34 are shown within the electrode package. Cables connecting these elements tot the defibrillator pass out of the package through gasket element 36 (shown diagrammatically as a dashed rectangle in the schematic). Each defibrillation electrode has a single electrical conductor 90 configured to carry a high voltage signal. Three shielded wires 92 connect to the three ECG monitoring electrodes (designated by the snap conductors 56 at the locations of the monitoring electrodes. Two wires 94 connect to the condition sensor 32 (although in a preferred embodiment the electrical conductors connecting to the condition sensor are shared with other wires (e.g., one or more of the CPR puck wires). Eight wires 96 connect to the CPR puck.

All of wires 90, 92, 94, and 96 pass through the gasket element 36, and extend to an electrode package connector 102 (electrodes end connector), which is plugged into the patient end connector 104 of a cable that runs back to the defibrillator. The two connectors 102, 104 are shown mated in FIG. 11.

An electronic memory device 100 (e.g., a Dallas Maxim semiconductor chip, Part No. DS2431) is built into connector 102. A variety of information is stored on the chip, including: an authentication code, a configuration code (e.g., whether the package contains ECG monitoring electrodes, a CPR puck, or only defibrillation electrodes), the type of electrodes (adult or pediatric), the expiration date of the electrode package, the serial number, and the date of manufacturing and manufacturing line. Other information (or less information) could be stored on the chip.

FIGS. 12-19 show the gasket element through which the electrical conductors extend. The gasket element is shown in perspective view in FIGS. 18 and 19. It has gradually tapered extensions 108 extending in the direction in which it is adhered to the perimeter of the seal between the rigid base 20 and removable lid 16 of the package 12. A bead 110 of silicone adhesive seals one surface of the gasket element to the rigid base 20 of the package. This material is chosen so that the gasket will part from the rigid base when the electrodes are removed from the base. Between the tapered extensions 108 is a central portion 112.

The gasket element has at least one surface exposed to the interior of the electrode package and at least one surface exposed to the exterior of the package. Holes pass through the gasket element from a surface exposed to the interior to a surface exposed to the exterior. Three electrical paths for the monitoring electrodes pass through three holes 120. Eight smaller holes 122 (or one narrow opening) provide access for the electrical paths connecting the CPR puck.

When the gasket releases from the rigid base of the electrode package, certain electrical connections can be broken. For example, a conductive shorting element 130 that shorts across the two high-voltage defibrillation wires 90 (to allow testing of the integrity of these electrical pathways outside of the electrical package) is broken away. A second electrical connection that is broken is the connection to the condition sensor. Wires 94 (or their equivalent) that provide electrical pathways to the metallic layers of the condition sensor are disconnected from the condition sensor. This is necessary because the condition sensor in this implementation remains in the electrode package, as its usefulness as a package condition sensor has ended with the opening of the package.

Various techniques could be used to accomplish the disconnection of these electrical connections when the gasket element is removed. In the implementation shown herein, conductive posts 150, extending upward from the rigid base of the package, and normally received in conductive apertures 152 (conically shaped to receive the posts) in the gasket element, withdraw from the apertures when the gasket is removed. the conductive posts shown are simply the ends of wires, bent 90 degrees to point upwardly, and stripped of insulation (the wider portion of the posts in the drawing is the wire with insulation; the narrower portion of the posts is the wire stripped of insulation). The conductive apertures (into which the posts extend) can be made from plated brass alloy with multiple fingers to engage the posts.

Figure 20:
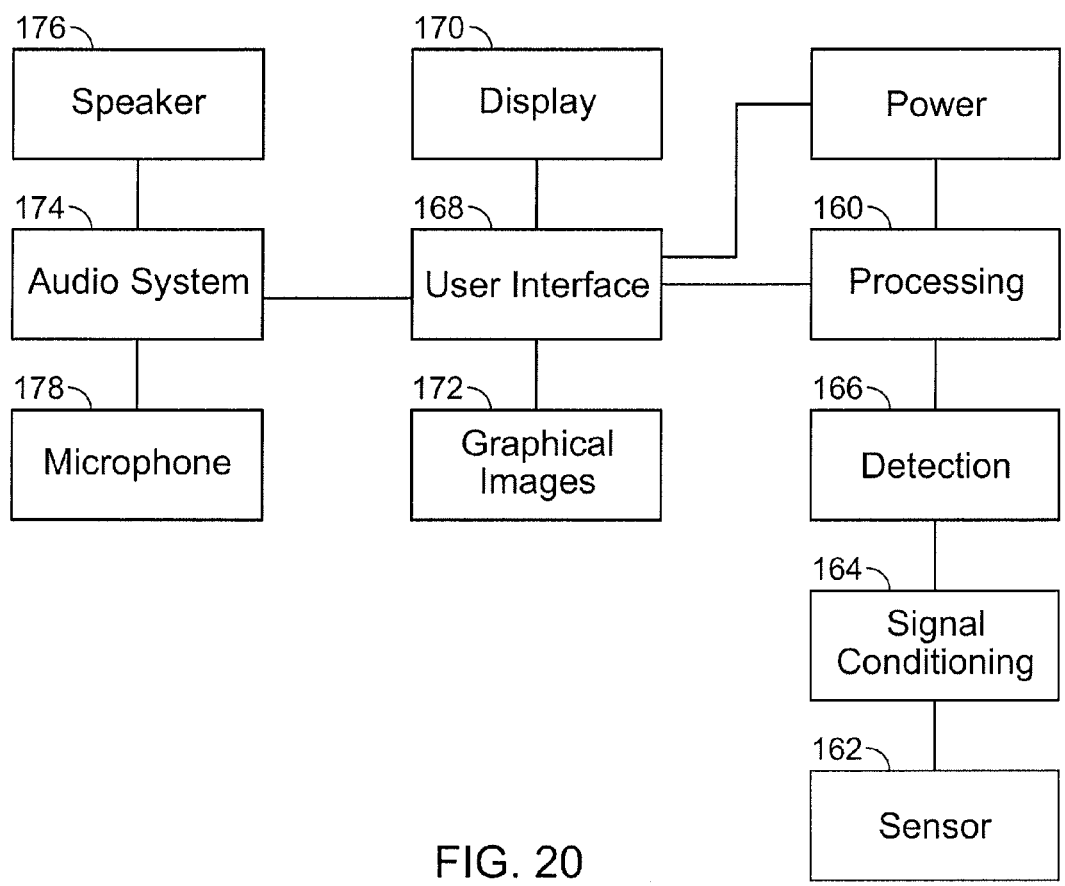
FIG. 20 is a block diagram of the electronics and components of the defibrillator of FIG. 1.

A general block diagram of the defibrillator is shown in FIG. 20. Processing circuitry and associated software (processing 160) is at the heart of the defibrillator. Inputs from sensors 162 such as the accelerometer in the CPR puck and the ECG monitoring electrodes on one of the electrode assemblies are received through signal conditioning and detection circuitry 164, 166. A user interface 168 provides outputs to a display 170 (and possibly to lights that direct the user to graphical images 172) and to an audio system 174 with speaker 176 and microphone 178.

Many other implementations other than those described above are within the invention, which is defined by the following claims. As mentioned earlier, it is not possible to describe here all possible implementations of the invention, but a few possibilities not mentioned above include the following: Not all of the features described above and appearing in some of the claims below are necessary to practicing the invention. Only the features recited in a particular claim are required for practicing the invention described in that claim. Features have been intentionally left out of claims in order to describe the invention at a breadth consistent with the inventors' contribution.

What is claimed is:

1. An electrode package for use with a defibrillator, the electrode package comprising:
   an outer shell providing a vapor barrier between an interior space inside the outer shell and an exterior environment;
   one or more defibrillation electrodes positioned in the interior space inside the outer shell;
   each of the defibrillation electrodes including a metallic layer in electrical contact with a conductive liquid-containing layer through which electrical current is delivered to a patient when the defibrillation electrodes have been applied to the patient, the conductive liquid-containing layer being subject to drying out as liquid from the water-containing layer vaporizes and travels from the interior space to the external environment; and
   one or more electrical conductors extending from inside of the outer shell to a package electrical connector outside of the shell, the package electrical connector being configured to be connected to a mating defibrillator electrical connector connected to the defibrillator, and
   an electronic memory device mechanically connected to the electrode package and positioned outside the outer shell and in electrical contact with some of the electrical conductors extending from the outer shell to the package electrical connector.

2. The package of claim 1 wherein the memory device is configured to store an expiration date for the electrode package.

3. The package of claim 1 wherein the memory device is positioned within the interior of the package electrical connector.

4. The package of claim 1 wherein the memory device is configured to store information indicative of a condition sensor voltage level at which the electrode may not be suited for defibrillation.

5. The package of claim 4 wherein the information stored by the memory device comprises a voltage threshold indicative of a limit on the acceptable electrical potential of an electrochemical cell within the electrode package.

6. The package of claim 1 wherein the memory device is configured to store an indication of whether the two defibrillation electrodes are therapeutic electrodes for use in delivery of defibrillation pulses or for use in training in the use of the defibrillator.

7. The package of claim 1 wherein the memory device is configured to store information that when read by the defibrillator can change the user interface or display provided the user of the defibrillator.

8. The package of claim 7 wherein the memory device is configured to store information indicative of the configuration of components inside the electrode package.

9. The package of claim 8 wherein the configurations identified by the information comprise: defibrillation electrodes only, defibrillation electrodes with ECG monitoring electrodes, defibrillation electrodes with CPR puck, and defibrillation electrodes with ECG monitoring electrodes and CPR puck.

10. The package of claim 8 wherein the information is indicative of prompts that should be delivered to the user.

11. The package of claim 1 wherein the memory device is configured to store information specifying a type of defibrillation electrode, wherein the type comprises whether the electrode is an adult or pediatric electrode.

12. An electrode package for use with a defibrillator, the electrode package comprising:
    an outer shell providing a vapor barrier between an interior space inside the outer shell and an exterior environment;
    one or more defibrillation electrodes positioned in the interior space inside the outer shell;
    each of the defibrillation electrodes including a metallic layer in electrical contact with a conductive liquid-containing layer through which electrical current is delivered to a patient when the defibrillation electrodes have been applied to the patient, the conductive liquid-containing layer being subject to drying out as liquid from the water-containing layer vaporizes and travels from the interior space to the external environment; and
    one or more electrical conductors extending from inside of the outer shell to a package electrical connector outside of the shell, the package electrical connector being configured to be connected to a mating defibrillator electrical connector connected to the defibrillator, and
    an electronic memory device mechanically connected to the electrode package and in electrical contact with some of the electrical conductors,
    wherein the memory device is configured to store information specifying a type of defibrillation electrode, wherein the type comprises whether the electrode is an adult or pediatric electrode.

13. The package of claim 12 wherein the memory device is further configured to store an indication of the configuration of components stored in the package.

14. The package of claim 12 wherein the memory device is further configured to store an expiration date for the electrode package.

15. An electrode package for use with a defibrillator, the electrode package comprising:
    an outer shell providing a vapor barrier between an interior space inside the outer shell and an exterior environment;
    one or more defibrillation electrodes positioned in the interior space inside the outer shell;
    each of the defibrillation electrodes including a metallic layer in electrical contact with a conductive liquid-containing layer through which electrical current is delivered to a patient when the defibrillation electrodes have been applied to the patient, the conductive liquid-containing layer being subject to drying out as liquid from the water-containing layer vaporizes and travels from the interior space to the external environment; and one or more electrical conductors extending from inside of the outer shell to a package electrical connector outside of the shell, the package electrical connector being configured to be connected to a mating defibrillator electrical connector connected to the defibrillator, and an electronic memory device mechanically connected to the electrode package and in electrical contact with some of the electrical conductors, wherein the memory device is configured to store information indicative of a voltage limit on the voltage output of a condition sensor indicating the functionality of the electrode.

16. The package of claim 15 wherein the information stored by the memory device comprises information indicative of a limit on an electrical potential of an electrochemical cell within the electrode package.

17. A defibrillator for providing a defibrillation pulse to electrodes applied to the chest of a patient, the defibrillator comprising a pair of electrical outputs for delivering the defibrillation pulse to a pair of defibrillation electrodes;

processing circuitry and associated software for controlling the defibrillator, including delivery of the defibrillation pulse;

an electrical energy storage element for storing the energy delivered in the defibrillation pulse;

a user interface element or elements connected to the processing circuitry for accepting one or more inputs from the user and communicating one or more pieces of information to the user; and a housing containing the storage element, processing circuitry, user interface, and providing at its exterior the pair of electrical outputs, wherein the processing circuitry and associated software are configured to read the content of a memory device mechanically connected to the electrode package and external to the defibrillator and associated with the pair of defibrillation electrodes, wherein the content comprises information specifying a type of defibrillation electrode, wherein the type comprises whether the electrode is an adult or pediatric electrode, and wherein the processing circuitry and associated software are configured to alter the energy level of the defibrillation pulse based on the type read from the memory device.

18. A defibrillator for providing a defibrillation pulse to electrodes applied to the chest of a patient, the defibrillator comprising a pair of electrical outputs for delivering the defibrillation pulse to a pair of defibrillation electrodes;

processing circuitry and associated software for controlling the defibrillator, including delivery of the defibrillation pulse;

an electrical energy storage element for storing the energy delivered in the defibrillation pulse;

a user interface element or elements connected to the processing circuitry for accepting one or more inputs from the user and communicating one or more pieces of information to the user; and a housing containing the storage element, processing circuitry, user interface, and providing at its exterior the pair of electrical outputs, wherein the processing circuitry and associated software are configured to read the content of a memory device mechanically connected to the electrode package and external to the defibrillator and associated with the pair of defibrillation electrodes, and wherein the content of the memory device is indicative of a limit on an electrical potential of a condition sensor within the electrode package.

19. The defibrillator of claim 18 wherein the limit represents a limit on the voltage output of the condition sensor for which a defibrillation pulse should be delivered.

20. The defibrillator of claim 19 wherein the condition sensor comprises an electrochemical cell and the limit represents the minimum electrical potential of the electrochemical cell.

21. The defibrillator of claim 20 wherein the processing circuitry and associated software are configured to compare a measured potential to the limit to call for delivery of a warning indication to the user based on the outcome of a comparison, wherein the warning indication informs the user that the defibrillation electrodes should be replaced.

22. A defibrillator for providing a defibrillation pulse to electrodes applied to the chest of a patient, the defibrillator comprising a pair of electrical outputs for delivering the defibrillation pulse to a pair of defibrillation electrodes;

processing circuitry and associated software for controlling the defibrillator, including delivery of the defibrillation pulse;

an electrical energy storage element for storing the energy delivered in the defibrillation pulse;

a user interface element or elements connected to the processing circuitry for accepting one or more inputs from the user and communicating one or more pieces of information to the user; and a housing containing the storage element, processing circuitry, user interface, and providing at its exterior the pair of electrical outputs, wherein the processing circuitry and associated software are configured to read the content of a memory device mechanically connected to the electrode package and external to the defibrillator and associated with the pair of defibrillation electrodes, and herein the content of the memory device is indicative of a user interface or prompt that should be provided to the user.

* * * * *